United States Patent [19]

Shapiro et al.

[11] Patent Number: 4,569,354
[45] Date of Patent: Feb. 11, 1986

[54] METHOD AND APPARATUS FOR MEASURING NATURAL RETINAL FLUORESCENCE

[75] Inventors: Jerrold M. Shapiro, Framingham; Jonathan M. Teich, Cambridge, both of Mass.

[73] Assignee: Boston University, Boston, Mass.

[21] Appl. No.: 360,385

[22] Filed: Mar. 22, 1982

[51] Int. Cl.[4] ............................................. A61B 6/08
[52] U.S. Cl. ................................... 128/665; 128/745
[58] Field of Search ....................... 128/633, 745, 665; 351/206, 207, 221; 250/461 B; 313/532

[56] References Cited

U.S. PATENT DOCUMENTS

| | | | |
|---|---|---|---|
| 3,157,812 | 11/1964 | Friedman et al. | 313/532 |
| 4,213,678 | 7/1980 | Pomerantzeff et al. | 351/7 |
| 4,231,750 | 11/1980 | Dowben | 250/459.1 |
| 4,368,047 | 1/1983 | Andrade et al. | 435/4 |
| 4,412,543 | 11/1983 | Vassiliadis et al. | 128/633 |

OTHER PUBLICATIONS

Furukawa et al., Optical Engineering, vol. 15, No. 4, pp. 321–324, Jul.–Aug. 1976.

*Primary Examiner*—Kyle L. Howell
*Assistant Examiner*—John C. Hanley
*Attorney, Agent, or Firm*—Hamilton, Brook, Smith & Reynolds

[57] ABSTRACT

Oxygenation of the retina is determined by measuring the fluorescence of flavoprotein in the retina. A spot of excitation light of a frequency of about 450 nanometers is scanned across the retina. Fluorescent light emitted from the retina at a frequency of about 520 nanometers is detected. The emission light may be detected at two frequencies of about 520 nm and 540 nm to allow for compensation for absorption and transmission variables in the eye. To compensate for fluoresence of the lens of the eye, the center of the pupil is imaged onto scanning mirrors so that the scanning beam of excitation light pivots at the center of the eye lens. Further, the center of the lens is imaged onto an optical stop in the emission optical path so that emitted light which passes back through the lens periphery, and not fluorescent light from the center of the lens, is detected. The emission light detector is a photon counting photomultiplier tube to permit safe limits on the intensity of the excitation light. Through computer controlled electronics, a fluorescent map can be stored in memory.

16 Claims, 9 Drawing Figures

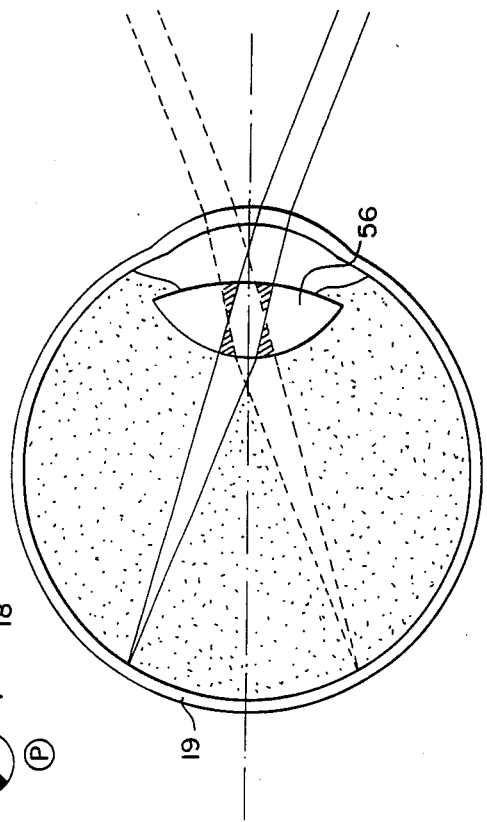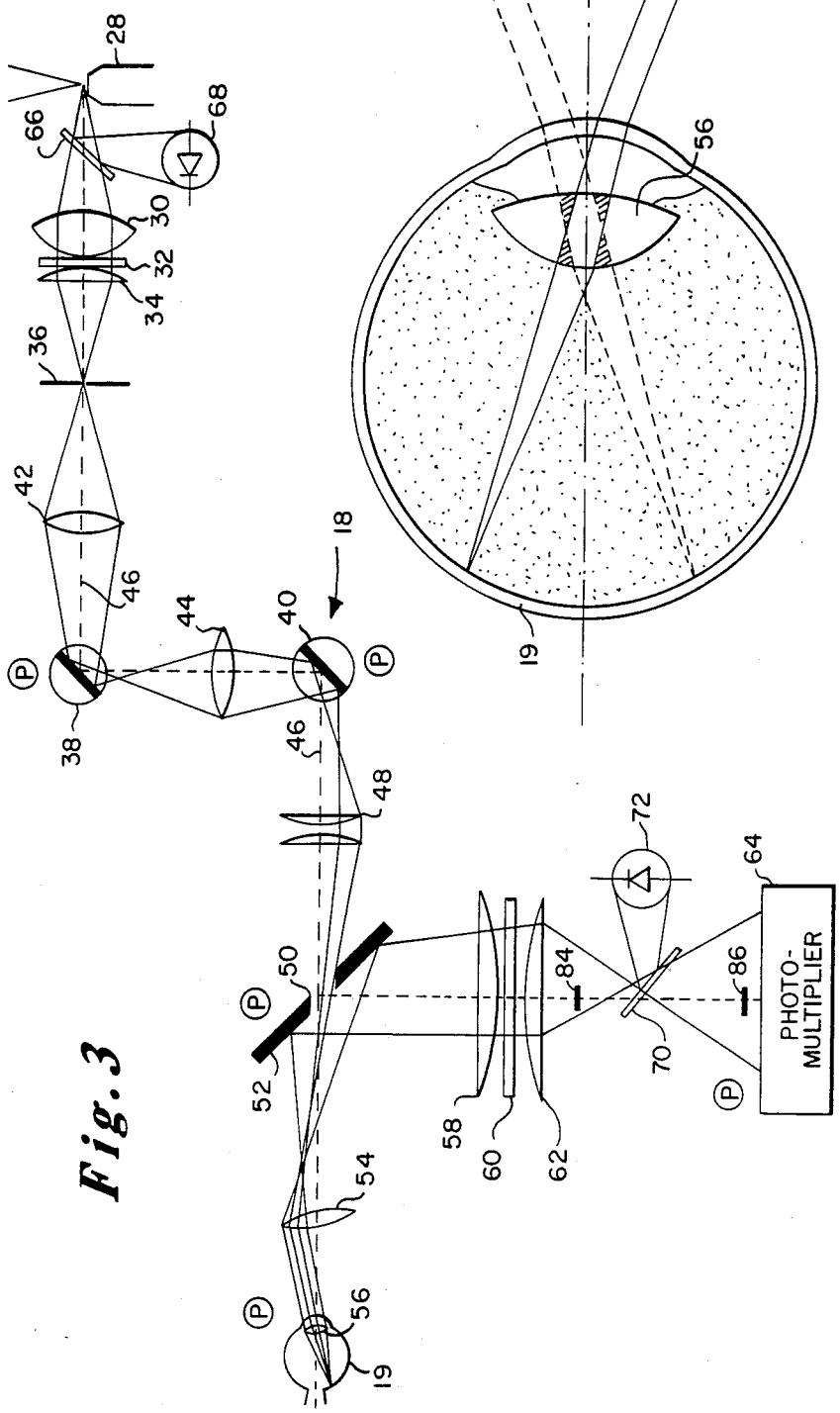

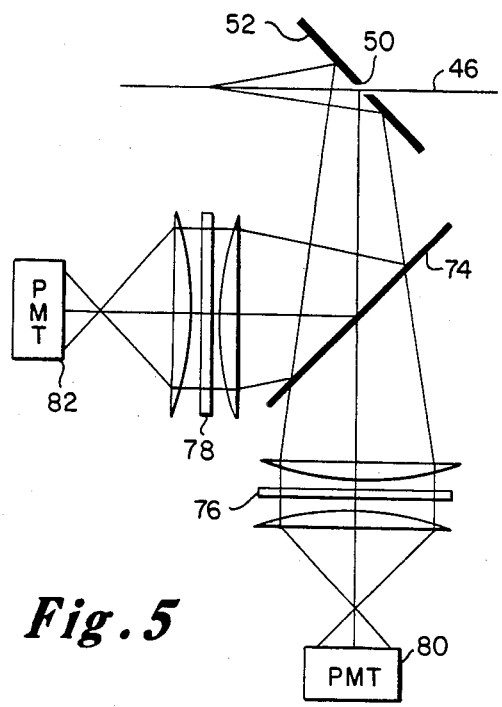
*Fig. 5*
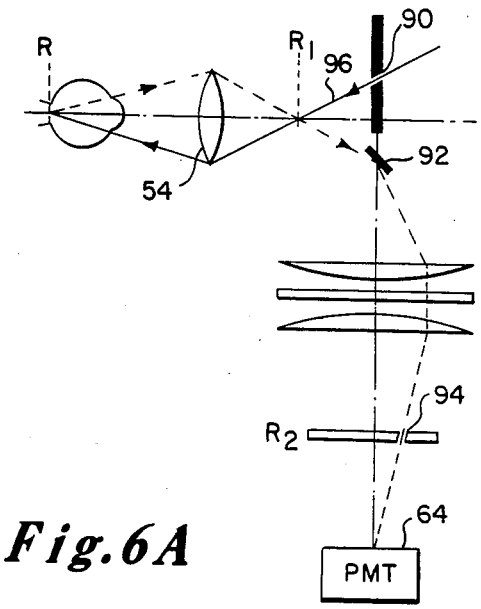
*Fig. 6A*
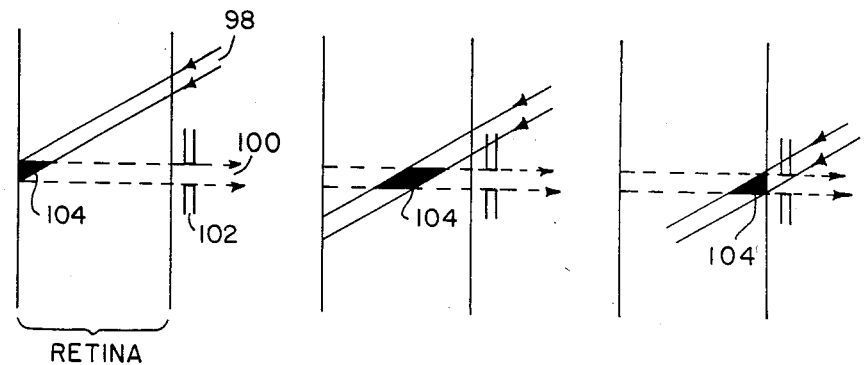
*Fig. 6B*  *Fig. 6C*  *Fig. 6D*

METHOD AND APPARATUS FOR MEASURING NATURAL RETINAL FLUORESCENCE

DESCRIPTION

1. Technical Field

This invention relates to measurement of the oxygenation of retinal tissue, and more particularly to a noninvasive method and apparatus for making such a measurement.

1. Background

Diabetic retinopathy is a major cause of visual loss in the United States. It can be divided into two broad stages: background and proliferative retinopathy. In background retinopathy, venous dilation and probably increased blood flow are present. Capillary micro- aneurysms, dot and blot hemorrhages, retinal edema, and hard exudates are found. Although edema of the macula can profoundly reduce vision, background retinopathy does not cause complete blindness. Cotton-wool spots, intraretinal microvacular abnormalities and a variety of venous abnormalities indicate a "pre-proliferative" phase of retinopathy. In proliferative retinopathy, microangiopathy impairs blood supply to the retina, depriving the retinal cells of oxygen, which is vital for proper nourishment. This condition is known as hypoxia. The body responds to poor blood flow by creating fibrous tissue and new blood vessels (neovascularization). These new blood vessels are very fragile and can bleed or hemorrhage into the vitreous, the clear, jelly-like substance that lies between the retina and the lens of the eye. This may cause sudden temporary loss of vision. After repeated extensive hemmorhaging, scar tissue can form. When this tissue retracts it can pull on the retina, causing it to detach. This may lead to permanent blindness.

Ophthalmologists now treat proliferative retinopathy with the argon laser in a procedure known as panretinal photocoagulation. The beam is applied to areas of the retina where hypoxia is thought to exist. The laser beam is applied in a scattered fashion to the entire retina. By reducing the amount of living tissue, the impaired blood supply is capable of supporting the remaining portion of the retina. Although patients often are left with a reduced visual field, they can function with central vision and the remaining visual field. Further visual acuity loss is slowed and neovascularization is usually reversed.

An object of this invention is to detect the location of the hypoxic areas of the retina in order to apply the laser beam exclusively to those areas. The procedure would be more selective, more effective, and would result in fewer side effects. A further object of the invention is to provide early detection of hypoxia for more successful treatment and less vision loss.

Previously, one could not readily measure poorly-oxygenated areas of the human retina. The only available method was highly invasive and involved inserting into the eye a very thin glass pipette with an ultra-fine point. A further object of this invention is to provide a noninvasive technique for measuring and mapping hypoxia on the retina.

The mitochondrial respiratory chain contains two components which fluoresce under appropriate stimulation: NADH and flavoproteins. Over the past thirty years, Britton Chance and his coworkers have shown that in a variety of tissues (liver, heart, kidney, brain), NADH fluorescence incteases, while flavoprotein fluorescence decreases, in a normoxic to anoxic transition.

Chance and others have been able to eliminate many artifacts due to the reflection and scattering of the excitation light by using the ratio of NADH, to flavoprotein fluorescence as their measure of oxygenation. However, the lens of the eye is interposed in the light pathway to and from the retina, and unfortunately, it strongly absorbs the ultraviolet excitation light for NADH and itself fluoresces.

A further object of this invention is to provide a device for measuring the fluorescence of the retina as an indication of the oxygenation of the retina.

DISCLOSURE OF THE INVENTION

In accordance with a preferred form of the invention, the retina is illuminated through a first portion of the eye's lens with light of a first, excitation frequency. Fluorescent light emitted by the retina at a second, emission frequency is detected through another portion of the eye's lens. An optical stop is provided in the emission light path at an image plane of the first portion of the eye's lens. In this way, fluorescence from the lens of the eye does not interfere with detection of fluorescence of the retina.

A spot of light is imaged on and scanned across the retina. That light is of a frequency which excites fluorescence in a substance in the retina. Light which fluorescences at a frequency other than the excitation frequency is detected. The detected signal is coordinated with the scanning movement of the spot of light to map the fluorescence of the retina. Preferably, the light detector is a photon counting photomultiplier tube. To detect the fluorescence of flavoprotein, the excitation light has a frequency of about 460 nanometers (nm) and the detected frequency is about 520 nm.

To minimize the effects of fluorescence of the crystalline eye lens through which both the excitation and fluorescent light must pass, each of two orthogonal scanning mirrors is imaged onto the center of the lens so that the scanning light beam pivots at the lens. In that way, the same small, interior portion of the eye lens is in the excitation light path throughout a scan and the fluorescence of the lens is substantially constant background noise. Further, the pupil of the eye is imaged near to a stop in the emission light path. That stop is preferably a hole in a pierced mirror. Thus fluorscent light from the illuminated central section of the eye lens does not reach the detector. Fluorescent light emitted from the retina passes through the periphery of the eye lens and bypasses the optical stop.

A reduction in the flavoprotein fluorescence with hypoxia may be offset by a larger amount of light incident on the flavoprotein due to a reduction in blood vessels. Thus, a normal amount of fluorescent light may be emitted from the retina even with low oxygen levels due to the lower level of absorption by the blood vessels. However, there is a color shift in the spectrum of the fluorescent light dependent on whether the flavoprotein is oxidized with high oxygen levels or reduced due to low oxygen levels. The amount of fluorescent light at each of those frequencies is dependent on the effect of blood vessels on transmission and that effect can be negated by calculating the ratio of the fluorescence of reduced flavoprotein to that of oxydized flavoprotein. To that end, the emitted light may be split and the divided light beams passed through separate filters and detected by separate photomultipliers. For flavoproteins, the detected frequencies are 520 nm and 540 nm.

The effects of blood vessels may also be compensated for by sequentially measuring the fluorescent light and reflected excitation light by rapidly changing the filter in the emission light path. To prevent detection of excitation light which may be reflected from an ophthalmoscope lens in the system, that lens is imaged into the plane of a small stop ahead of the photomultiplier tube. Similarly, to avoid detection of light scattered by a pierced mirror, that mirror is imaged onto a small optical stop in front of the photomultiplier tube.

In processing the signal provided by the photomultiplier tube, photons detected by the tube are counted during a time interval corresponding to a small segment of a line of scan. Movement of the scanning spot during that segment of time defines a pixel in a final mapping of the fluorescence. After the spot scans a pixel, a high speed counter which counts the photomultiplier output is reset to count the photons in the next pixel.

In the preferred scanning control, the location of each scan line is stored in digital memory. The scanning of a line is controlled by a circuit which responds to computer inputs indicating rate of scan, length of scan and position of a controlling point within the scan line.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3 is an optical schematic of the optical components of the system of FIG. 1; and FIG. 4 is a cross sectional view of an eye illustrating the pivotal effect of the scanning light beam at the eye lens;

FIG. 5 illustrates a split emission light path for detecting fluorescent light at two frequencies;

FIG. 6 illustrates a system in which slit illumination locates the depth of fluorescence within the retina.

PREFERRED EMBODIMENT OF THE INVENTION

Figure 1:
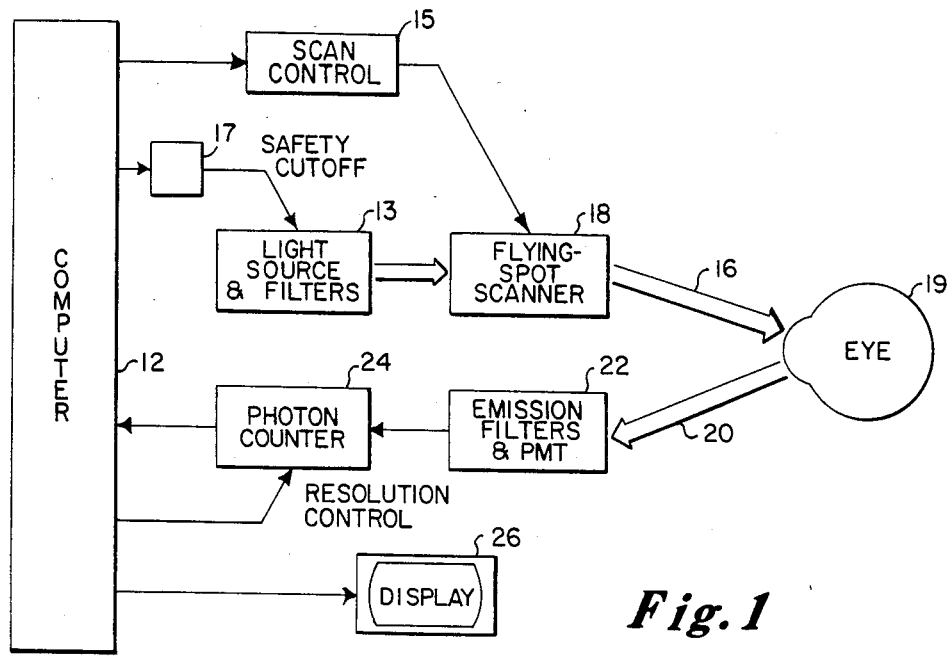
FIG. 1 is a block diagram of a preferred embodiment of the invention.

A system for illuminating the retina of an eye and detecting fluorescent light from the retina and for subsequently providing a map of the fluorescent light is shown in a simplified block diagram of FIG. 1. The system is controlled by a computer 12 and associated electronics. Electronic boards 15, 17 and 24 function as independent satellite controllers which receive instructions from and direct data to the computer.

The nonelectronic hardware of the system comprises a mercury arc lamp light source 13 which transmits light through the lens of an eye 19 onto the retina of the eye through and optical path 16. The optical path includes lenses and mirrors and a set of motor driven mirrors forming a flying spot scanner 18. Through the optical path 16, including the flying spot scanner 18, an image of a light spot is formed on and scanned across the retina, preferably in a raster scan. In a raster scan, the imaged light spot is moved rapidly along successive lines on the retina and is sequentially stepped from line to line.

In a preferred system, the light source and filters 13 provide blue light of a frequency of about 450 nm. As shown in FIG. 2A, light in the range of about 380 nm to 470 nm will excite flavoproteins to fluoresce. As shown in FIG. 2B the fluorescent light is primarily within a range of about 500 nm to 580 nm and has a peak at about 520 nm. That light is passed through an emission optical path 20 through emission filters to a photomultiplier tube 22. The emission filters block out the blue excitation light so that the photomultiplier tube detects only the green fluorescent light. Photons which impinge on the cathode of the photomultiplier tube are counted in photon counter electronics 24.

About 13% of the photons which strike the photomultiplier tube cause the photomultipliers associated electronics to send a pulse to the counter 24. The counter is a high speed, 100 million counts per second, electronic counter that is interfaced to the computer. The computer also controls the speed of scan by the flying spot scanner 18 through scan control 15. By counting photons throughout short time segments of each scan line and resetting the counter after each segment, the scan line can be divided into a number of pixels. The final count of the counter before resetting specifies the number of photons received by the photomultiplier tube within that pixel of the scan line. For example, to define 50 pixels, or picture elements, within a scan line, the counter is reset 50 times during the scan while the imaged spot moves rapidly across the retina. Each pixel count of photons is stored in the computer's memory for computation or for display on a video display 26. The data thus stored in computer memory provides an accurate map of fluorescent light from the retina.

A detailed optical schematic of the system is shown in FIG. 3. Light from the mercury arc lamp 28 is collimated by a lens 30 and passed through an excitation filter 32. Although flavoproteins fluoresce most when excited by light of about 450 nm, the mercury arc lamp emits a substantially greater portion of its light at a frequency of 436 nm. That frequency is still well within the range of frequencies which will excite the flavoproteins, and light at about that frequency is passed through the filter 32. The filtered blue light is focused by lens 34 through a pinhole 36. The image of the pinhole 36 is ultimately focused onto the retina of the eye 19. First, however, scanning of the light beam from the pinhole is induced by a flying spot scanner 18 comprising mirrors 38 and 40. The pinhole is imaged just beyond the mirror 38 by a lens 42 and just beyond the mirror 40 by a lens 44. Lens 44 also forms on image of mirror 38 on mirror 40.

The mirrors 38 and 40 are shown in a single plane. However, the scanner is a three dimensional system. Each mirror is mounted on a horizontal axis of rotation which is perpendicular to the excitation optic axis 46. The axes of rotation are orthogonal to each other so that one causes scanning of the light beam in one direction and the second causes scanning of the light beam in an orthogonal direction. As is conventional with flying spot scanners, additional mirrors may be provided to direct the optic axis in any desired direction. The mirror 38 scans rapidly at a constant speed as it forms each line of the scan. After each such scan of mirror 38, mirror 40 is incremented so that the next scan of mirror 38 forms a scan line spaced from the first.

Movement of the scanning mirrors 38 and 40 is controlled by scan control electronics 15. Those electronics receive signals from the computer 12 indicative of the rate of scan, length of scan and center position of the scan lines. The computer also provides precise position location for each line of the scan. The scan control electronics 15 then operate independently of the computer causing the spot to scan rapidly along a line and back on the same line. Return of the spot triggers stepping to the next line and the scan is re- peated.

The scanning light beam from the scanner 18 is focused by lenses 48 through a hole 50 in a pierced mirror 52. The scanning spot is imaged through an ophthalmoscope lens 54 and the crystalline lens 56 of the eye onto the retina. Most of the blue excitation light is reflected from the retina back through the pupil. However, a small portion of that light excites fluorescence of the flavoproteins in the retina. The fluorescent light is shifted in frequency from the excitation light. That fluorescent light is emitted back through the crystalline lens 56 and ophthalmoscope lens 54. Some of that emission light is lost through the hole 50 but a substantial portion is reflected by the mirror 52 along an emission optical path. That light is collimated by a lens 58 and directed through an emission filter 60. The filter 60 passes the green fluorescent light of about 520 nm but blocks the blue excitation light. The filtered light is then focused and directed toward a photomultiplier 64 by the lens 62. As previously described, the photomultiplier provides a count of photons which impinge on its cathode.

A primary problem in detecting the fluorescent light from the retina is that the crystalline lens 56 also fluoresces. To avoid detection of that light, each of the scanning mirrors 38 and 40 is imaged onto a small central portion of the pupil. The eye's pupil is the area of the crystalline lens that is not covered by the iris. (The image planes where the pupil is imaged throughout the system are indicated by the reference letters P.) As a result, there is an optical pivot of the scanning beam at the center of the crystalline lens as illustrated in FIG. 5. The center of the crystalline lens is imaged onto the hole 50 in the pierced mirror so that a substantial portion of the fluorescent light from the lens 56 passes harmlessly through the hole 50 back into the excitation optical path.

- FIG. 4 is a section of the eye showing the scanning beam of light at its extreme positions. Because the image of the scanning mirrors and of the hole 50 are imaged onto the crystalline lens, the beam is restricted to the center of the lens throughout the scan. At the center of the lens, the thickness of the lens seen by the beam of light is near constant. Further, the diamond shaped region near the center of the lens is common to the two paths shown in FIG. 4, and its absorption and scattering will effect both beams in the same way. As a result, any fluorescent light from the crystalline lens 56 which reaches the photomultiplier will be viewed as a constant background in the finally collected data.

The system includes several safeguards to protect the eye of the patient and the sensitive photomultiplier. A beam splitter 66 reflects a very small portion of the excitation light from the lamp 28 onto a photodiode 68. If the light received by the photodiode exceeds a preset threshold, a shutter in front of the light source closes and the power to the arc lamp is shut off. Also, if the current through the diode 68 drops below a preset level, it is assumed that the diode is not functioning properly and the shutter closes and the lamp is shut off. A similar beam splitter 70 in front of the photomultipler directs a small portion of the emission light toward a photodiode 72. The voltage applied to the photomultiplier is turned off in the event that the signal on the photodiode exceeds or drops below preset levels.

The velocities of the scanning motors are also monitored. If either motor runs too slowly, thereby increasing the time that light illuminates each part of the retina, the shutter in front of the light source closes and power to the arc lamp is interupted. The shutter is normally closed so that, if it has no power or it somehow fails, it will normally close. All of the safety monitors continue functioning even when the computer itself fails. The computer can set upper and lower limits for each variable monitored and can determine which component failed if any variable is outside its specified range.

The instrument illuminates the eye with a 5 microwatt beam of light from the mercury arc lamp. The beam is focused to, typically, a diameter of 0.133 mm on the retina, and the focused spot is typically swept over a twenty-two degree field every 0.15 seconds. It is quite comfortable and useful to view the scanning beam continuously.

The safety of the instrument is evaluated by assuming that all the light which enters the eye is focused on the retina, and that the beam is viewed continuously for periods of up to one minute. At present, the light beam is swept left to right, then returned to the left along the same line before it is lowered to the next line of the raster scan; each pixel within the scanned area is illuminated twice during each scan. At present, a square fifty pixels on a side is scanned every 0.25 seconds. The energy received by each pixel is equal to the product of the power in the illuminating beam and the average duration of the beam over the spot: 5 microwatts times 0.25 seconds per raster divided by $2 \times 50 \times 50$ points per raster equals 0.025 nanojoules per pixel. A 0.133 mm diameter pixel has an area of 0.00014 square centimeters, and is illuminated within an energy of 1.8 microjoules per square centimeter. For continuous viewing at four complete scans per second, each pixel receives an average of 7.2 microwatts per square centimeter, which is far below the maximum safe level.

The number of photons emitted from each pixel is counted. In the human eye, with a 0.133 mm diameter spot, we are collecting and detecting 2500 photons per pixel. In the dark, without the patient in place, we detect 1 or 2 counts per pixel. Since the standard deviation in the number of photons counted is the square root of the average count (2500), or 50 in this case, the coefficient of variation of the fluorescence measurements is 50/2500 times 100 percent, or two percent. The instrument is very flexible and can increase the number of photons collected per scan point by a facter of 64; this would reduce the coefficient of variation of the fluorescence measurements to 0.25 percent.

Because a low level of light is used to protect the patient, a very sensitive light detector is required. Twenty-five percent of the exciting light and 20 percent of the fluorescent light is absorbed by the ocular media (cornea crystalline lens, aqueous and vitreous tumors). Light is also lost through the hole in the pierced mirror and due to absorbtion by the emission filter. For every two hundred million photons going into the eye, only one will be measured. We therefore use the most sensitive light measurement to count individual photons. We direct $10^{12}$ photons at each pixel of retina we study; for the largest spot used, this corresponds to 0.4 microjoules on each 0.4 millimeter diameter spot, or 0.32 microjoules per square centimeter. This level is about a factor of 700 below the maximum safe light level on the retina. About 2500 photons are detected from each pixel.

The instrument has great flexibility, and has a scanning spot size that can be varied from 15 to 400 um in diameter, and a field of view which can be as small as two spot diameters or as large as the field of view of available indirect ophthalmoscope lenses, 45 to 60 degrees. The upper limit on spot size was chosen so that the instrument could resolve photocoagulation scars. In practice, the field of view is chosen small enough that a complete scan can be completed in the time between eye blinks.

Another difficulty encountered in measuring the fluorescence of flavoprotein is that other chemicals, including blood pigment, absorb light in the color range of excitation and fluorescence. Because the hypoxic areas may also have fewer blood vessels, less excitation light may be absorbed in those areas. As a result, the decreased fluorescence of the flavoproteins might be offset by increased excitation light in those regions. To compensate for such changes in absorption and transmission within the eye, the system of FIG. 4 can be utilized.

Figure 2:
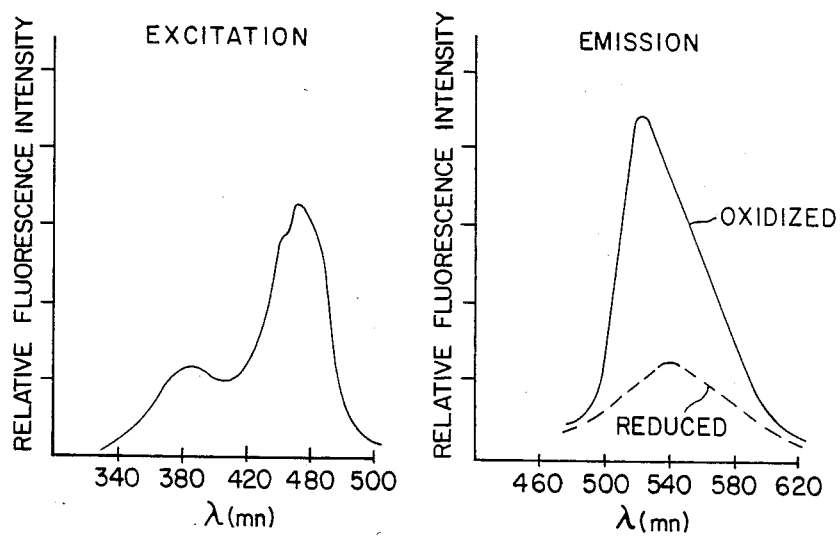
FIGS. 2A and 2B illustrate the excitation and emission spectra for flavoprotein.

The system of FIG. 2 is based on the assumption that all of the fluorescent light from the flavoprotein is of a single frequency. In fact, flavoproteins have a different emission spectra depending on whether they are oxidized or reduced. In well oxygenated areas (normoxic retina), the flavoproteins will be oxydized, but where hypoxia exists some of the flavoproteins will be in a reduced form. In the system of FIG. 5, a beam splitter 74 is provided to direct some of the emission light to each of two filters 76 and 78. One filter passes light in the frequency range of the fluorescence of reduced flavoprotein and the other passes light of a frequency range emitted by oxidized flavoprotein. The light which passes through these filters is detected by respective photomultipliers 80 and 82. The ratio of oxidized flavoprotein to the total amount of flavoprotein, the redox state of the flavoprotein, can then be calculated. Factors which are common to both, including transmission characteristics of the eye, absorption characteristics, and excitation light intensity are cancelled out in this ratio.

Yet another method of compensating for the absorption in the eye would be to obtain a measure of the amount of blue light reflected from the retina and then normalize the green light signal to that measure of reflected light. To that end, several emission filters 60 are mounted on a wheel equipped with a high speed rotation mechanism so that, for each pixel, a reading of green light can be obtained and then a reading of blue light can be obtained. Thus, for example, during a first raster scan, one filter would be in the optical path and the filter would be quickly changed for a second raster scan of the same portion of the retina. Separate counts of detected light would be made by counter 24 for each color at each pixel.

In using light reflected from the retina to normalize the detected signal, the emission filter 60 does not block out spurious blue light while reflected light is detected. Spurious light might be reflected from the lenses 54 and 56, primarily from their centers, and from the edge of hole 50 in the mirror 52. Such optical artifacts are removed by appropriately placed stops. For example, light reflected by the cornea is focused back through the hole 50 in the pierced mirror and does not enter the detection path. A similar process occurs with light reflected by the crystalline lens surfaces and that backscattered from its interior. The image of the scanning mirrors is 2.5 mm in size at the center of the pierced mirror; the hole is 3.5 mm in diameter. The lenses 58 and 62 on either side of the emission filter 60 form an image of the hole 50 in the pierced mirror on the photocathode of the photomultiplier. An opaque dot 86 of a nonfluorescent material is placed near the photocathode and centered on the image of the hole to block light scattered by the edge of the hole. The ophthalmoscope lens reflects some light into the detection path, mainly from the small part of its surface that is perpendicular to the optical axis. The lenses 58 and 60 near the emission filter form an image of the ophthalmoscope lens in a plane between them and the photomultiplier; a small stop 84 in this plane blocks the light reflected by the ophthalmoscope lens.

Another potential problem for sensing flavoprotein fluorescence is that the retina has two sources of oxygen, the choroidal and retinal circulations. The choroidal circulation supplies oxygen mainly to the outer retina, while the retinal circulation supplies the inner retina. Diabetes affects mainly the inner retinal circulation. Thus, one observes decreased flavoprotein fluorescence from the inner retina over a background of essentially normal fluorescence from the outer retina. The percentage change in flavoprotein fluorescence from inner retinal disease alone may thus be too small to be reliably detected. This could produce a false negative result (i.e. hypoxic regions might go undetected). One way to resolve this is to use oblique slit illumination of the retina. The slits generate optic sections of the retina. This allows separate collection of light from the inner and outer retina to make independent measurements from these areas.

In the event that fluorescence from the outer retina masks fluorescence from the inner retina, the optical system can be modified to generate the optic sections of the retina as shown in FIG. 6.

The apparatus is modified by replacing the pierced mirror with a narrow slit 90 about one millimeter wide centered in the image of the scanning mirrors, moving the optical axis of the eye and ophthalmoscope lens down about six millimeters, moving the light detection optics and photomultipler 64 down about twelve millimeters, placing a small mirror 92 (about 1.5 mm in diameter) on the optical axis of the light detection optics and approximately twelve millimeters below the center of the slit in the illumination path, and by placing a narrow slit 94 about 25 micrometers wide in front of the photomultiplier tube in the plane of the image of the retina R2.

A ray of illuminating light, shown as a solid line 96, passes through the illumination slit 90, retinal plane R1, ophthalmoscope lens 54, and the ocular media until it reaches the retina, R. As shown in FIGS. 6B to 6D, this ray of light only excites fluorescent substances in the retina that lie within the light beam. The slit 94 in front of the photomultiplier is imaged onto the retina to form a slit image 102, and only light that originates from the part of the retinal tissue between the dashed lines in FIGS. 6B–D reaches the photomultipliers. The optics are arranged so that the illumination light enters the eye about six millimeters above the place where the light exits the eye. There is an angle between the illumination beam 98 and viewing beam 100 as shown in the figures. The two beams intersect within the retinal tissue to form a diamond shape 104. Only light from within this diamond, shown shaded in FIGS. 6B-D, contributes to the measured fluorescence.

FIGS. 6B-D show the location of the diamond shape 104 for three positions of the scanning beam 98. In the first case, B, the diamond shape is located in the outer retina, and measures primarily the fluorescence from mitochondria in the photoreceptors. A short time later, the beam is lower, C, and the diamond shape is in the middle of the retina. Still later, the beam has moved down further, D, and the diamond shape is located in the inner retina, and we are measuring fluorescence from the part of the retina most affected by diabetic retinopathy. To study various locations on the retina, the patient can either rotate his/her eye, or mirror 92 can be mounted on a galvanometer motor shaft and pivoted about an axis perpendicular to the paper.

The data is processed by rapidly reading the photon counter as the illumination beam is swept back and forth in the vicinity of the image of slit 94. For example, collect data as the beam sweeps downward in the figure. The reading will be zero until the illumination beam 98 intersects the viewing beam 100. The first nonzero reading will be from the outer retina, while the last non-zero reading will be from the inner retina. The location of the diamond shape within the retina at any given time can be calculated from knowledge of the scanning speed, the angle within the eye between the illuminating and viewing beams, and the optical magnification between the planes R and R2.

While the invention has been particularly shown and described with references to a preferred embodiments thereof, it will be understood by those skilled in the art that various changes in form and details may be made therein without departing from the spirit and scope of the invention as defined by the appended claims. For example, fluorescence other than the natural fluorescence of flavoprotein may be measured. As an example, fluorescence of Cytochrome-C, which fluoresces in the red, may be measured. Also, means for separating the excitation and emission optic paths other than the pierced mirror can be used.

We claim:

1. Apparatus for determining the natural fluorescence of the retina of the eye comprising:
   excitation means in an excitation optic path along an excitation optic axis for imaging and scanning a spot of light of an excitation frequency of about 450 nanometers across the retina; and
   emission detection means comprising a photon counting photomultiplier tube in an emission optic path along an emission optic axis for detecting fluorescent light from the retina at two emission frequencies of about 520 nanometers, to the exclusion of light at the excitation frequency, and providing respective emission signals; and
   electronic means responsive to the respective emission signals for generating an output emission signal as a function of the relative magnitudes of the respective emission signals.

2. Apparatus for determining the fluorescence of the retina of an eye comprising:
   excitation means in an excitation optic path along an excitation optic axis for imaging and scanning a spot of light of an excitation frequency across a retina;
   emission detection means for independently detecting fluorescent light from the retina at at least two emission frequencies to the exclusion of light at the excitation frequency and providing respective emission signals, and
   electronic means responsive to the respective emission signals for generating an output emission signal as a function of the relative magnitudes of the respective emission signals to provide an indication of the fluorescence of the retina.

3. Apparatus as claimed in claim 2 wherein the emission detection means detects light having emission frequencies of about 520 nanometers and 540 nanometers.

4. Apparatus for determining the fluorescence of the retina of the eye comprising:
   excitation means in an excitation optic path along an excitation optic axis for imaging and scanning a spot of light from a scanning beam of an excitation frequency across the retina, the excitation means including means for pivoting the beam of light about a point in the middle of the lens thickness such that the beam passes through substantially the same interior portion of the eye lens throughout scan of the retina;
   emission detection means in an emission optic path along an emission optic axis for detecting fluorescent light emitted from the retina at at least two emission frequencies, to the exclusion of light at the excitation frequency, the emission detection means comprising a photon counting photomultiplier and means for summing the photomultiplier output for each of the emission frequencies during successive units of time corresponding to successive small segments of spot scan and electronic means for generating an output emission signal as a function of the relative magnitudes of detected fluorescent light at the two frequencies; and
   means for coordinating the output emission signal with scanning movement of the spot of light to provide a fluorescent map of the retina comprising pixels corresponding to said small segments of spot scan.

5. Apparatus as claimed in claim 4 wherein the excitation means scans light having an excitation frequency of about 450 nanometers and the emission detection means detects light at emission frequencies of about 520 nanometers and 540 nanometers.

6. Apparatus as claimed in claim 4 wherein the means for pivoting the beam of light comprises means for imaging the lens of the eye onto each of two scanning mirrors and the emission detection means comprises means for optically stopping reflected excitation light from the cornea and fluorescent light emitted by the lens in the emission optic path.

7. Apparatus as claimed in claim 4 further comprising a central processor means for providing a line position indication to set the location of each line of the scan and wherein the excitation means comprises a fast scanning mirror and an orthogonally disposed slow scanning mirror and means for incrementing the slow scanning mirror in response to the fast scanning mirror and the line position indication.

8. Apparatus as claimed in claim 7 further comprising a central processor means for providing rate of scan, length of scan and position of scan indications and a scan control circuit for causing the fast scanning mirror to scan continuously between increments of the slow scanning mirror based on the rate of scan, length of scan and position of scan indications received by the scan control circuit from the central processor.

9. Apparatus as claimed in claim 8 comprising a central processor means for providing rate of scan, length of scan and position of scan indications and a scan control circuit for causing the fast scanning mirror to scan based on the rate of scan, length of scan and position of scan indications received by the scan control circuit from the central processor.

10. Apparatus as claimed in claim 4 wherein the excitation optic axis and emission optic axis intersect at a mirror which forms an optical stop in the emission optic axis, the optical stop being imaged onto a small optical stop in the emission optic path to minimize detection of light reflected by the first optical stop from the excitation optic path.

11. Apparatus as claimed in claim 4 comprising an ophthalmoscope lens common to both the excitation optic path and the emission optic path and means for optically stopping excitation light reflected from said ophthalmoscope lens in the emission light path.

12. A method of measuring the oxygenation of the retina of an eye comprising:

imaging and scanning a spot of light of an excitation frequency across the retina, the excitation frequency being such that it excites natural fluorescence of a material of the retina at in at least one emission frequency indicative of the oxygenation of the retina, the spot of light being scanned across the retina by directing a beam of light through the lens of the eye and pivoting the beam about a point in the middle of the lens thickness such that the beam passes through substantially the same interior portion of the eye lens throughout scan; and detecting the amplitude of fluorescent light of the at least one emission frequency emitted from the retina at to the exclusion of light at the excitation frequency and measuring the oxygenation of the retina as a function of the amplitude found in said step of detecting.

13. A method as claimed in claim 12 comprising scanning a spot of light having an excitation frequency of about 450 nanometers and detecting emitted light having an emission frequency of about 520 nanometers.

14. A method as claimed in claim 12, wherein the step of detecting comprises detecting the amplitude of fluorescent light at two different emission frequencies, and the step of measuring comprises measuring the oxygenation of said retina as a function of the relative amplitudes found in said step of detecting.

15. A method as claimed in claim 14 wherein the detected emission frequencies are about 520 nanometers and 540 nanometers.

16. A method as claimed in claim 12 further comprising the step of generating a fluorescent map of pixels, each pixel being formed by summing the light detected during a segment of a spot scan.

* * * * *